(12) United States Patent
Markson et al.

(10) Patent No.: US 11,379,979 B2
(45) Date of Patent: Jul. 5, 2022

(54) COMPUTER IMAGING PRE-PROCESSING FOR AUTOMATED MEDICATION DISPENSING ANALYSIS

(71) Applicant: Express Scripts Strategic Development, Inc., St. Louis, MO (US)

(72) Inventors: Christopher R. Markson, Hawthorne, NJ (US); Pritesh J. Shah, Paramus, NJ (US); Christopher G. Lehmuth, St. Louis, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 16/998,358

(22) Filed: Aug. 20, 2020

(65) Prior Publication Data
US 2021/0004958 A1    Jan. 7, 2021

Related U.S. Application Data

(63) Continuation of application No. 16/190,548, filed on Nov. 14, 2018, now Pat. No. 10,776,916.
(Continued)

(51) Int. Cl.
*G06T 7/00* (2017.01)
*G06T 7/70* (2017.01)
(Continued)

(52) U.S. Cl.
CPC .............. *G06T 7/0012* (2013.01); *G06T 7/12* (2017.01); *G06T 7/13* (2017.01); *G06T 7/70* (2017.01);
(Continued)

(58) Field of Classification Search
CPC ........ G16H 20/10; G16H 40/20; G16H 70/40; G16H 10/60; G16H 40/67; G16H 20/17; G16H 40/63; G16H 30/20; G16H 30/40; G16H 40/60; G16H 50/20; G16H 80/00; G16H 15/00; G16H 20/00; G16H 20/13;
(Continued)

(56) References Cited

U.S. PATENT DOCUMENTS 5,597,995 A   1/1997 Williams
6,226,081 B1  5/2001 Fantone
(Continued)

FOREIGN PATENT DOCUMENTS

EP      05236642 A    1/1993

*Primary Examiner* — Golam Sorowar
(74) *Attorney, Agent, or Firm* — Miller Johnson

(57) ABSTRACT

A computer system includes an input configured to receive a first image of medication located in a receptacle, memory, and a processor configured to execute instructions including creating a second image based on the first image, dividing pixels of the second image into first and second subsets, and scanning the second image along a first axis to count, for each point along the first axis, a number of pixels in the first subset along a line perpendicular to the first axis that intersects the first axis at the point. The instructions also include estimating positions of first and second edges of the receptacle along the first axis based on the counts of the pixels, defining an opening of the receptacle based on the estimated positions of the first and second edges, and outputting a processed image that indicates areas of the image that are outside of the defined opening.

20 Claims, 11 Drawing Sheets

Related U.S. Application Data

(60) Provisional application No. 62/590,255, filed on Nov. 22, 2017.

(51) Int. Cl.
*G06T 7/13* (2017.01)
*G06T 11/00* (2006.01)
*G16H 20/13* (2018.01)
*G06T 7/12* (2017.01)
*G16H 30/40* (2018.01)

(52) U.S. Cl.
CPC .......... *G06T 11/001* (2013.01); *G16H 20/13* (2018.01); *G16H 30/40* (2018.01); *G06T 2207/20076* (2013.01); *G06T 2207/20081* (2013.01); *G06T 2207/30242* (2013.01)

(58) Field of Classification Search
CPC ...... G07F 17/0092; G07F 11/44; G07F 11/00; G07F 11/165; G07F 9/002; G07F 11/52; G07F 11/70; G07F 9/026; G07F 11/58; G07F 5/18; G07F 7/00; G07F 9/023; B65G 1/1378; B65G 1/1373; B65G 2201/0261; B65G 11/203; B65G 1/00; B65G 1/06; B65G 2201/0235; B65G 2201/0258; B65G 43/08; B65G 47/42; B65G 47/44; B65G 47/904; B65G 1/1376; A61J 7/0084; A61J 2205/30; A61J 1/03; A61J 7/02; A61J 2205/10; A61J 2205/60; A61J 7/0418; A61J 7/0481; A61J 3/00; A61J 7/0454; A61J 1/035; A61J 2200/30; A61J 7/04; A61J 1/05; A61J 2200/70; A61J 2205/20; A61J 2205/40; A61J 7/0427; A61J 7/0436
See application file for complete search history.

(56) References Cited

U.S. PATENT DOCUMENTS

| | | | |
|---|---|---|---|
| 6,535,637 B1* | 3/2003 | Wootton | B65B 57/00 382/190 |
| 6,621,928 B1 | 9/2003 | Inagaki | |
| 7,409,085 B2 | 8/2008 | Hu | |
| 7,844,118 B1 | 11/2010 | Li | |
| 7,995,831 B2 | 8/2011 | Eller | |
| 8,756,998 B1 | 6/2014 | Joplin | |
| 9,978,036 B1 | 5/2018 | Eller | |
| 10,023,341 B1 | 7/2018 | Christopher | |
| 2003/0204357 A1* | 10/2003 | Hamilton | G06K 9/00 702/128 |
| 2004/0150734 A1 | 8/2004 | Sobel | |
| 2006/0104534 A1 | 5/2006 | Rai | |
| 2008/0056556 A1 | 3/2008 | Eller | |
| 2009/0232397 A1 | 9/2009 | Hara | |
| 2009/0324090 A1 | 12/2009 | Tanaka | |
| 2010/0310178 A1 | 12/2010 | McCandlish | |
| 2015/0243027 A1 | 8/2015 | Ichiki | |

* cited by examiner

COMPUTER IMAGING PRE-PROCESSING FOR AUTOMATED MEDICATION DISPENSING ANALYSIS

CROSS-REFERENCE TO RELATED APPLICATIONS

This application is a continuation of U.S. application Ser. No. 16/190,548, which was filed Nov. 14, 2018 and which claims the benefit of priority to U.S. Provisional Application No. 62/590,255, filed Nov. 22, 2017. The entire disclosures of these applications are incorporated herein by reference.

FIELD

The present disclosure relates to image processing and, more particularly, to image pre-processing that excludes irrelevant features from further image processing steps.

BACKGROUND

A pharmacy may process and fill a large number of prescriptions from prescription orders. Automatic systems may be used by a high-volume pharmacy to process and fulfill prescriptions. Errors in filling a prescription, such as when the wrong medication is dispensed or when multiple medications are erroneously combined, are very difficult to detect. Human checking is very expensive and suffers from all the fragilities of human abilities. For example, a human's attention may be diverted, the human's attention may decrease over time, and the human eye may not be sensitive to certain discrepancies in dispensed medication.

However, training a computer to recognize dispensing errors with medication is very difficult. Recognizing the myriad ways in which medication can be dispensed and the innumerable angles at which individual medication items may be arranged in the dispensed product poses a significant challenge to computer algorithms. Further, computer algorithms may have difficulty differentiating between the dispensed medication and the package into which the medication was dispensed. For these reasons, many pharmacies do not use automated review of every dispensed medication, and, instead, rely on human spot checks of a small (often, random) subset of dispensed medications.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A machine includes a camera configured to capture a first image of medication held by a receptacle. The machine includes memory hardware that stores code and processor hardware that executes the code stored by the memory hardware. The code implements a color processing module configured to create a second image based on the first image in which each pixel of the second image is identified by a single value. The code implements a pixel identification module configured to divide pixels of the second image into first and second mutually exclusive subsets of pixels. Pixels of the first subset are more likely to correspond to the receptacle than are pixels of the second subset. The code implements a scanning module configured to process the second image along a first axis by, for each point along the first axis: defining a line that is perpendicular to the first axis and intersects the first axis at the point; counting how many of the pixels in the second image located along the line are in the first subset; and recording the count. The code implements a maxima detection module configured to determine a first local maximum of the counts and a second local maximum of the counts. The code implements an elliptic calculation module configured to estimate a position of a first edge of the receptacle based on a position of the first local maximum along the first axis, estimate a position of a second edge of the receptacle based on a position of the second local maximum along the first axis, and define an ellipse based on the first and second edges. The code implements an output module configured to output a processed image based on the first image. The processed image indicates that areas of the first image that are outside the defined ellipse are excluded from further processing.

In other features, the color processing module is configured to, for each pixel of the first image, generate a corresponding pixel of the second image exclusive of any other pixels of the first image. In other features, the color processing module is configured to, for each pixel of the first image, generate the corresponding pixel of the second image by calculating a grayscale value of the pixel. In other features, the color processing module is configured to, for each pixel of the first image, generate the corresponding pixel of the second image by: setting a green value of the corresponding pixel to a sum of a green value of the pixel and a blue value of the pixel minus a red value of the pixel; setting a green value of the corresponding pixel to zero; and setting a blue value of the corresponding pixel to zero.

In other features, the output module is configured to include metadata with the processed image. The metadata identifies the areas of the first image that are excluded from further processing. In other features, the output module is configured to set the areas of the first image that are excluded from further processing to a black color. In other features, the maxima detection module is configured to determine the first local maximum within a first region of the second image and determine the second local maximum within a second region of the second image. The first region and the second region are non-overlapping. A third region of the second image is nonzero in size, does not overlap the first region, and does not overlap the second region.

In other features, the scanning module is configured to process the second image along a second axis by, for each point along the second axis: defining a line that is perpendicular to the second axis and intersects the second axis at the point; counting how many of the pixels in the second image located along the line are in the first subset; and recording the count. The code further implements a second maxima detection module configured to determine a first local maximum of the counts for the second axis and a second local maximum of the counts for the second axis. The elliptic calculation module is configured to: estimate a position of a third edge of the receptacle based on a position of the first local maximum along the second axis; estimate a position of a fourth edge of the receptacle based on a position of the second local maximum along the second axis; and define the ellipse based on the first, second, third, and fourth edges.

In other features, the first axis is parallel to a first edge of the first image and the second axis is perpendicular to the first axis. In other features, the elliptic calculation module is configured to, in response to the second local maximum being less than the first local maximum by more than a predetermined amount, estimate the position of the second edge of the receptacle to be an edge of the first image.

A method includes capturing a first image of medication held by a receptacle. The method includes creating a second image based on the first image in which each pixel of the second image is identified by a single value. The method includes dividing pixels of the second image into first and second mutually exclusive subsets of pixels. Pixels of the first subset are more likely to correspond to the receptacle than are pixels of the second subset. The method includes processing the second image along a first axis by, for each point along the first axis: defining a line that is perpendicular to the first axis and intersects the first axis at the point; counting how many of the pixels in the second image located along the line are in the first subset; recording the count. The method includes determining a first local maximum of the counts and a second local maximum of the counts. The method includes estimating a position of a first edge of the receptacle based on a position of the first local maximum along the first axis. The method includes estimating a position of a second edge of the receptacle based on a position of the second local maximum along the first axis. The method includes defining an ellipse based on the first and second edges. The method includes outputting a processed image based on the first image. The processed image indicates that areas of the first image that are outside the defined ellipse are excluded from further processing.

In other features, the creating the second image includes, for each pixel of the first image, generating a corresponding pixel of the second image exclusive of any other pixels of the first image. In other features, the creating the second image includes, for each pixel of the first image, generating the corresponding pixel of the second image by: setting a green value of the corresponding pixel to a sum of a green value of the pixel and a blue value of the pixel minus a red value of the pixel; setting a green value of the corresponding pixel to zero; and setting a blue value of the corresponding pixel to zero.

In other features, the method includes including metadata with the processed image. The metadata identifies the areas of the first image that are excluded from further processing. In other features, the method includes setting the areas of the processed image that are excluded from further processing to a black color. In other features, the first local maximum is determined within a first region of the second image. The second local maximum is determined within a second region of the second image. The first region and the second region are non-overlapping. A third region of the second image is nonzero in size, does not overlap the first region, and does not overlap the second region.

In other features, the method includes processing the second image along a second axis by, for each point along the second axis: defining a line that is perpendicular to the second axis and intersects the second axis at the point; counting how many of the pixels in the second image located along the line are in the first subset; and recording the count. The method includes determining a first local maximum of the counts for the second axis and a second local maximum of the counts for the second axis. The method includes estimating a position of a third edge of the receptacle based on a position of the first local maximum along the second axis. The method includes estimating a position of a fourth edge of the receptacle based on a position of the second local maximum along the second axis. The method includes defining the ellipse based on the first, second, third, and fourth edges.

In other features, the first axis is parallel to a first edge of the first image and the second axis is perpendicular to the first axis. In other features, the method includes, in response to the second local maximum being less than the first local maximum by more than a predetermined amount, estimating the position of the second edge of the receptacle to be an edge of the first image.

A non-transitory computer-readable medium stores instructions that include capturing a first image of medication held by a receptacle. The instructions include creating a second image based on the first image in which each pixel of the second image is identified by a single value. The instructions include dividing pixels of the second image into first and second mutually exclusive subsets of pixels. Pixels of the first subset are more likely to correspond to the receptacle than are pixels of the second subset. The instructions include processing the second image along a first axis by, for each point along the first axis: defining a line that is perpendicular to the first axis and intersects the first axis at the point; counting how many of the pixels in the second image located along the line are in the first subset; and recording the count. The instructions include determining a first local maximum of the counts and a second local maximum of the counts. The instructions include estimating a position of a first edge of the receptacle based on a position of the first local maximum along the first axis. The instructions include estimating a position of a second edge of the receptacle based on a position of the second local maximum along the first axis. The instructions include defining an ellipse based on the first and second edges. The instructions include outputting a processed image based on the first image. The processed image indicates that areas of the first image that are outside the defined ellipse are excluded from further processing.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Figure 1:
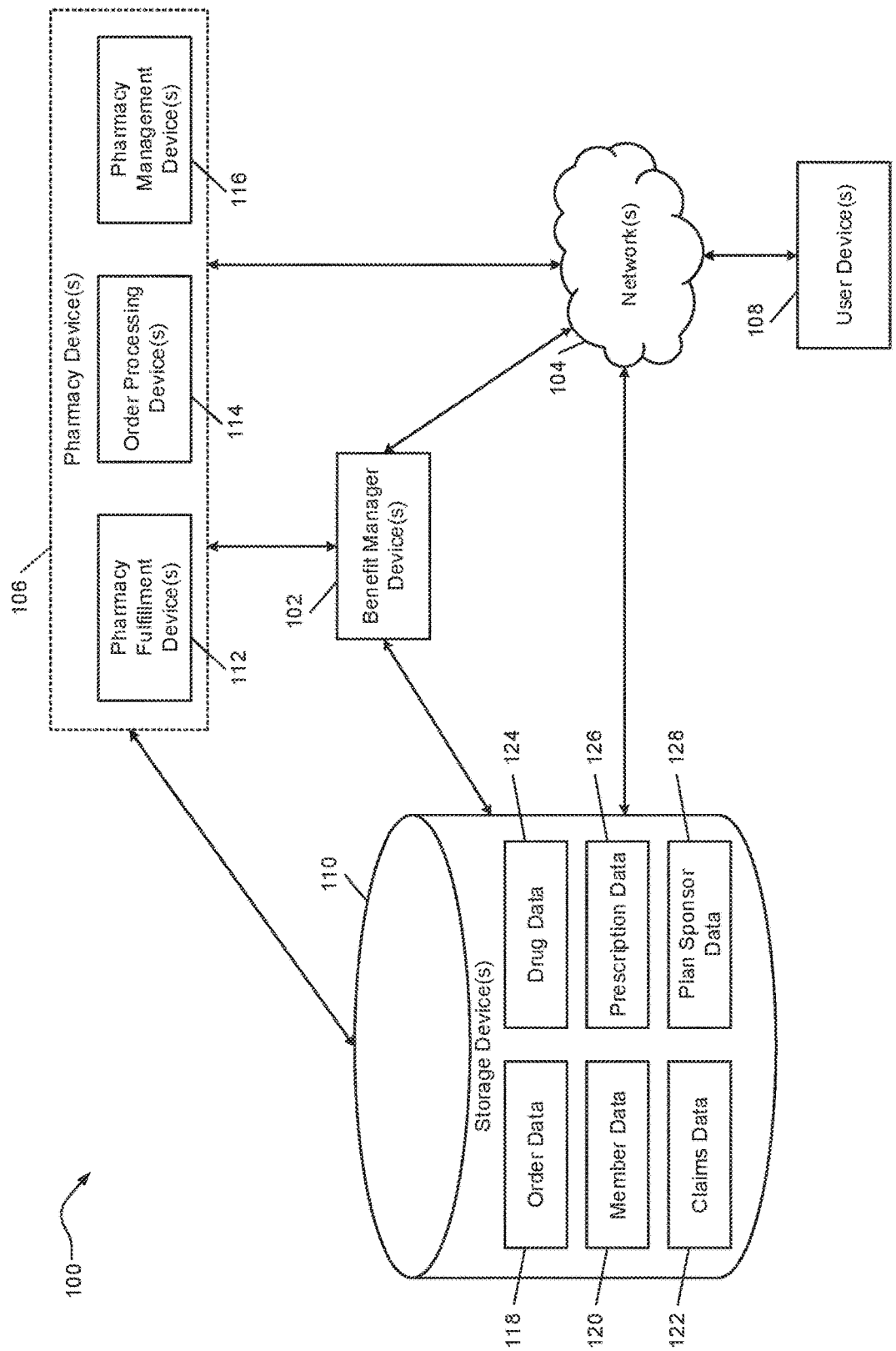
FIG. 1 is a functional block diagram of a sample implementation of a system for a high-volume pharmacy.

Example systems and methods for computer imaging pre-processing for automated medication dispensing analysis in, for example, a pharmacy, are described. Generally, a prescription order is generated for a high-volume pharmacy. The prescription order may include more than one prescription drug for fulfillment. Each prescription drug in a prescription order is an order component of the prescription order. Generally, the order components are pill bottles, liquid bottles, blister packs, unit-of-use packs, injectable package, spray bottles, tubes, ampoules, drop counters, insulated boxes, child-resistant containers, or other packaging having a quantity of a prescription drug contained therein.

While the medications described in this disclosure will be referred to as prescription drugs, the principles of the present disclosure also apply to nonprescription medications. Further, while various receptacles are capable of receiving prescription drugs, the present disclosure will focus on the example container being a cylindrical bottle. In general terms, dispensing equipment dispenses prescription drugs according to a prescription order into a bottle (sometimes referred to as a pill bottle). To ensure that the correct drugs are dispensed into the bottle, including that no unexpected prescription drugs are included (even a single one), a photo is taken from above the bottle. The photo is processed to determine a confidence level that the prescription drugs in the bottle match the prescription order and do not include any unexpected prescription drugs.

Many factors affect the quality of the image, such as lighting, camera position with respect to the bottle, camera angle with respect to the bottle, cleanliness of the lens of the camera, etc. Further, across different dispensing lines and different dispensing facilities, the hardware set-up may not be identical. Additionally, each image will generally include some areas outside the bottle or, if the imaged area is reduced, portions of the bottle itself may be omitted in the image. Before automatic image analysis can proceed, preprocessing may be performed to identify the edges of the bottle. Once the edges of the bottle are identified, image analysis can ignore areas outside of the bottle. Moreover, the preprocessing may exclude some or all of the bottle so that image processing can focus only on the prescription drugs.

By enhancing the contrast or performing other color processing, the bottle may generally show up with the darkest pixels. Once the darkest pixels in the image are identified, the image is analyzed column by column. With the knowledge that the bottle will be circular or at least elliptic, the first third and last third of the image are analyzed to attempt to identify the edges of the bottle. The left third of the image is analyzed to identify a likely left edge of the pill bottle while the right third is analyzed to identify a likely right edge of the pill bottle.

The highest number of dark pixels per column will occur at the edge of the bottle. The highest number of dark pixels, therefore, establishes the edge of the bottle. If the highest number of pixels in the first third and last third are too different, the edge with a much lower peak number of pixels may actually be outside the borders of the image. The edge's absence in the image explains why the peak number of dark pixels is so much lower.

After analyzing the image column by column, the analysis switches to row by row to establish the top and bottom edges of the pill bottle. Once the four edges are defined, an ellipse is calculated based on the locations of the edges. Everything outside the ellipse may be excluded from further analysis. Applying this preprocessing may significantly reduce the number of false positives in which the machine vision system believes an unwanted prescription drug was dispensed into the bottle. The preprocessing may also reduce false negatives where an unwanted prescription drug is present in the bottle but is not identified.

High-Level Block Diagram

FIG. 1 is a block diagram of an example implementation of a system 100 for a high-volume pharmacy, according to an example embodiment. While the system 100 is generally described as being deployed in a high-volume pharmacy or a fulfillment center (e.g., a mail order pharmacy, a direct delivery pharmacy, etc., and the like), the system 100 and/or components thereof may otherwise be deployed (e.g., in a lower volume pharmacy, etc.). A high-volume pharmacy may be a pharmacy that is capable of filling prescriptions automatically, mechanically, manually, or a combination thereof. The system 100 may include a benefit manager device 102, a pharmacy device 106, and a user device 108 in communication with each other directly and/or over a network 104. The system may also include a storage device 110.

The benefit manager device 102 is a device operated by an entity that is at least partially responsible for creation and/or management of the pharmacy or drug benefit. While such entity operating the benefit manager device 102 is typically a pharmacy benefit manager (PBM), other entities may operate the benefit manager device 102 on behalf of themselves (i.e., the PBMs) or other entities. For example, the benefit manager device 102 may be operated by a health plan, a retail pharmacy chain, a drug wholesaler, a data analytics, or other type of software-related company, etc., or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, etc., and the like. The PBM may, in addition to its PBM operations, operate one or more than one pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store, etc.) from a pharmacist or a pharmacist technician. The member may also obtain the prescription drug through mail order drug delivery from a mail order pharmacy location, which may be the system 100. In some embodiments, the member may obtain the prescription drug directly or indirectly through the use of a machine, such as a kiosk, vending unit, mobile electronic device, or a different type of mechanical, electrical, electronic communication device and/or computing device. Such a machine may be filled with the prescription drug in prescription packaging, which may include multiple prescription components, by the system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, etc., or the like. In some instances, an employer of the member may directly or indirectly fund or reimburse the member for the copayments.

The amount of the copayment required by the member may vary with different pharmacy benefit plans having different plan sponsors or clients and/or for different prescription drugs. The member's copayment may be a flat copayment (e.g., $10, etc.), co-insurance (e.g., 10%, etc.), and/or a deductible (e.g., for first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels used for the prescription drug to be received. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM, e.g., the benefit manager device 102, may perform certain adjudication operations including verifying eligibility for the member, identifying/reviewing an applicable formulary for the member to determine any appropriate copayment, coinsurance, and deductible for the prescription drug, and performing a drug utilization review (DUR) on the member. Further, the PBM may provide a response to the pharmacy, e.g., the pharmacy system 100, following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However in some instances, these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on types of pharmacy network in which the pharmacy is included. In some embodiments, the amount may also be determined based on other factors. For example, if the member pays the pharmacy for the prescription drug without using the prescription or drug benefit provided by the PBM, the amount of money paid by the member may be higher than when the member uses the prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102-110 or in parallel to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy device 106 may be utilized by the pharmacy to submit the claim to the PBM for adjudication.

Additionally, in some embodiments, the pharmacy device 106 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager device 102 may track prescription drug fulfillment and/or other information for patients that are not members or have not identified themselves as members, at the time (or in conjunction with the time) in which they seek to have a prescription filled at a pharmacy.

The pharmacy device 106 may include an order processing device 114, a pharmacy management device 116, and a pharmacy fulfillment device 112 in communication with each other directly and/or over the network 104.

The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the pharmacy fulfilment device 112. In some embodiments, the order processing device 114 may be an external order processing device separate from the pharmacy and communicate with other devices located within the pharmacy.

For example, the external order processing device may communicate with an internal pharmacy order processing device and/or other devices located within the system 100. In some embodiments, the external order processing device may have limited functionality (e.g., as operated by a patient requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together. In some embodiments, the order processing device 114 may operate in combination with the pharmacy management device 116.

The order processing device 114 may include circuitry, a processor, a memory to store data and instructions, and communication functionality. The order processing device 114 is dedicated to performing processes, methods and/or instructions described herein. Other types of electronic devices specifically configured to implement with the processes, methods and/or instructions described herein may also be used.

In some embodiments, at least some functionalities of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage, etc.) and/or through the network 104 (e.g., by utilizing a cloud configuration or software as a service. etc.) with the storage device 110.

The user device 108 is used by a device operator. The device operator may be a user (e.g., an employee, a contractor, a benefit member, etc.) associated with a software development project. Other device operators may also operate the user device 108.

The user device 108 may be a stand-alone device that solely provides at least some of the functionality to enable analysis of software development risks, or may be a multi-use device that has functionality outside of analysis of software development risks. Examples of the user device 108 include a set-top box (STB), a receiver card, a mobile telephone, a personal digital assistant (PDA), a display device, a portable gaming unit, and a computing system, etc. Other devices, however, may also be used. In some embodiments, the computing system may include a mobile computing device. For example, the user device 108 may include a mobile electronic device, such an iPhone or iPad by Apple, Inc., mobile electronic devices powered by Android by Google, Inc., and a Blackberry by Research In Motion Limited. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, etc.) in communication with the benefit manager device 102, the pharmacy device 106, and/or the user device 108 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (e.g., drug name and strength, etc.) and quantity of the prescription drug, etc. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 118 may be used by a high volume fulfillment center to fulfill a pharmacy order.

In some embodiments, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as bar code data read from pallets, bins, trays, carts, and the like used to transport prescriptions within the pharmacy may also be stored as order data 118.

The member data 120 includes information regarding the members associated with the PBM. The information stored as member data 120 may include personal information, personal health information, protected health information, and the like. Examples of the member data 120 include name, address, telephone number, e-mail address, prescription drug history, etc., and the like. The member data 120 may include a plan sponsor identifier that identifies the plan sponsor associated with the member and/or a member identifier that identifies the member to the plan sponsor. The member data 120 may include a member identifier that identifies the plan sponsor associated with the patient and/or a patient identifier that identifies the patient to the plan sponsor. The member data 120 may also include, by way of example, dispensation preferences such as type of label, type of cap, message preferences, language preferences, or the like.

The member data 120 may be accessed by various devices in the pharmacy, (e.g., the high volume fulfillment center, etc.), to obtain information utilized for fulfillment and shipping of prescription orders. In some embodiments, an external order processing device operated by or on behalf of a member may have access to at least a portion of the member data 120 for review, verification, etc., or other purposes.

In some embodiments, the member data 120 may include information for persons who are patients of the pharmacy but are not members in the pharmacy benefit plan being provided by the PBM. For example, these patients may obtain drug directly from the pharmacy, through a private label service offered by the pharmacy, the high volume fulfillment center, or otherwise. In general, the use of the terms member and patient may be used interchangeably herein.

The claims data 122 includes information regarding pharmacy claims adjudicated by the PBM under a drug benefit program provided by the PBM for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, GPI number, medication class, the cost of the prescription drug provided under the drug benefit program, the copay/coinsurance amount, rebate information, and/or member eligibility, etc. Additional information may be included.

In some embodiments, other types of claims beyond prescription drug claims may be stored in the claims data 122. For example, medical claims, dental claims, wellness claims, or other type of health care-related claims for members may be stored as a portion of the claims data 122.

In some embodiments, the claims data 122 includes claims that identify the members with whom the claims are associated. In some embodiments, the claims data 122 includes claims that have been de-identified (e.g., associated with a unique identifier but not with a particular, identifiable member, etc.).

The drug data 124 may include drug name (e.g., technical name and/or common name, etc.), other names by which the drug is known by, active ingredients, an image of the drug (e.g., in pill form, etc.), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc., and the like.

Figure 2:
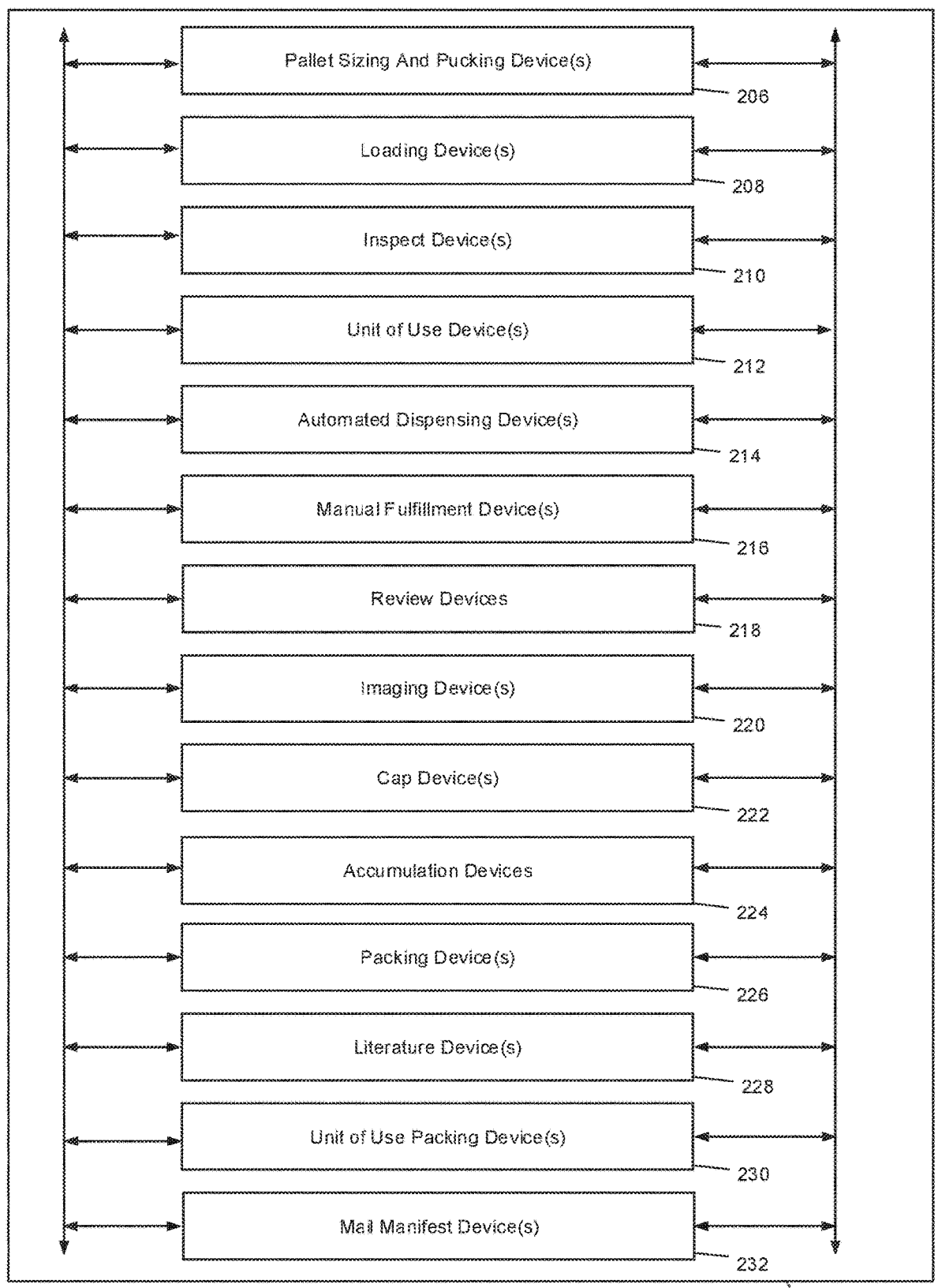
FIG. 2 is a functional block diagram of an example pharmacy fulfillment device that may be deployed within the system of FIG. 1, according to an example embodiment.

FIG. 2 illustrates the pharmacy fulfillment device 112, according to an example embodiment. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some embodiments, operations performed by one of these devices 206-232 may be performed sequentially, or in parallel with the operations of another device as may be coordinated by the order processing device 114. In some embodiments, the order processing device 114 tracks a prescription with the pharmacy based on operations performed by one or more than one devices 206-232.

In some embodiments, the pharmacy fulfillment device 112 may transport prescription drug containers, for example, between more than one of the devices 206-232 in the high volume fulfillment center, by use of pallets. The pallet sizing and pucking device 206 may configure pucks in a pallet. A pallet may be a transport structure for a number of prescription containers, and may include a number of cavities. A puck may be placed in one or more than one the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism, or the like. In one embodiment, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations, (e.g., at the high volume fulfillment center, etc.).

The inspect device 210 may verify that containers in a pallet are correctly labeled and in the correct spot on the pallet. The inspect device 210 may scan the label on one or more than one containers on the pallet. Labels of containers may be scanned or imaged in full or in part by the inspect device 210. Such imaging may occur after the container has been lifted out of its puck by a robotic arm, picker, etc., or the like, or may be otherwise scanned or imaged while retained in the puck. In some embodiments, images and/or video captured by the inspect device 210 may be stored in the storage device 110 as order data 118.

The unit of use device 212 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like. Prescription drug products dispensed by the unit of use device 212 may be packaged individually or collectively for shipping, or may be shipped in combination with other prescription drugs dispensed by other devices in the high volume fulfillment center.

At least some of the operations of devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more than one devices that dispense prescription drugs or pharmaceuticals into prescription containers in accordance with one or multiple prescription orders. In general, the automated dispensing device 214 may include mechanical and electronic components with, in some embodiments, software and/or logic to facilitate pharmaceutical dispensing that would otherwise be performed in a manual fashion by a pharmacist and/or pharmacist technician. For example, the automated dispensing device 214 may include high volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high volume fulfillment center.

The manual fulfillment device 216 may provide for manually fulfillment of prescriptions. For example, the manual fulfillment device 216 may receive or obtain a container and enable fulfillment of the container by a pharmacist or pharmacy technician. In some embodiments, the manual fulfillment device 216 provides the filled container to another device in the pharmacy fulfillment devices 112 to be joined with other containers in a prescription order for a patient or member. In general, a manual fulfillment may include operations at least partially performed by a pharmacist or a pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter, etc.). Prescription drugs dispensed by the manual fulfillment device 216 may be packaged individually or collectively for shipping, or may be shipped in combination with other prescription drugs dispensed by other devices in the high volume fulfillment center.

The review device 218 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, and the like. In an example, the manual review can be performed at the manual station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114, and/or stored in the storage device 110 as part of the order data 118.

The cap device 222 may be used to cap or otherwise seal a prescription container. In some embodiments, the cap device 222 may secure a prescription container with a type of cap in accordance with a patient preference (e.g., a preference regarding child resistance, etc.), a plan sponsor preference, a prescriber preference, or the like. The cap device 222 may also etch a message into the cap, although this process may be performed by a subsequent device in the high volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218, at the high volume fulfillment center. The accumulation device 224 may be used to group the prescription containers prior to shipment to the member or otherwise.

The literature device 228 prints, or otherwise generates, literature to include with prescription drug orders. The literature may be printed on multiple sheets of substrates, such as paper, coated paper, printable polymers, or combinations thereof. The literature printed by the literature device 228 may include information required to accompany the prescription drugs included in a prescription order, relating to prescription drugs in the order, financial information associated with the order (e.g., an invoice or an account statement, etc., or the like).

In some embodiments, the literature device 228 folds or otherwise prepares the literature for inclusion with a prescription drug order (e.g., in a shipping container, etc.). In some embodiments, the literature device 228 that prints the literature may be separate from the literature device that prepares the literature for inclusion with a prescription order.

The packing device 226 packages a prescription order in preparation for shipping the order. The packing device 226 may box, bag, or otherwise package the fulfilled prescription order for delivery. The packing device 226 may further place inserts, (e.g., literature or other papers, etc.), into the packaging received from the literature device 228 or otherwise. For example, bulk prescription orders may be shipped in a box, while other prescription orders may be shipped in a bag which may be a wrap seal bag.

The packing device 226 may label the box or bag with an address and a recipient's name. The label may be printed and affixed to the bag or box, be printed directly onto the bag or box, or otherwise associated with the bag or box, etc. The packing device 226 may sort the box or bag for mailing in an efficient manner (e.g., sort by delivery address, etc.). The packing device 226 may include ice or temperature sensitive elements for prescriptions which are to be kept within a temperature range during shipping in order to retain efficacy or otherwise. The ultimate package may then be shipped through postal mail, through a mail order delivery service that ships via ground and/or air (e.g., UPS, FEDEX, or DHL, etc.), through delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example embodiment, the manual scanning may be performed at a manual station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232 multiple devices may be used. The devices 206-232 may be the same type or model of device or may be different device types or models. When multiple devices are present, the multiple devices may be of the same device type or models or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (e.g. by conveyors, etc.), networked, and/or otherwise in contact with one another or integrated with one another, (e.g., at the high volume fulfillment center, etc.). In addition, the functionality of a device may be split among a number of discrete devices and/or combined with other devices.

Figure 3:
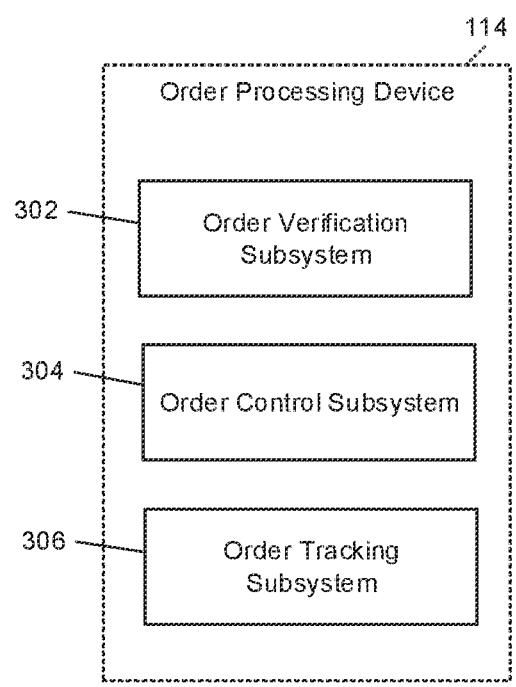
FIG. 3 is a functional block diagram of an example order processing device that may be deployed within the system of FIG. 1, according to an example embodiment.

FIG. 3 illustrates the order processing device 114, according to an example embodiment. The order processing device 114 may be used by one or more than one operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR. Other communications between the order verification subsystem 302 and the benefit manager device 102 may be performed for a variety of purposes.

The order control subsystem 304 controls various movements of the containers and/or pallets along with various filling functions during their progression through the system 100. In some embodiments, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors to deliver the pallet from the loading device 208 to the manual fulfillment device 216, for example, from the literature device 228 to deliver paperwork as needed to fill the prescription.

The order tracking subsystem 306 may track a prescription order as it progresses (or stops) toward fulfillment. The order tracking subsystem 306 may track, record and/or update order history, order status, or the like. The order tracking subsystem 306 may store data locally (e.g., in a memory, etc.) or as a portion of the order data 118 stored in the storage device 110.

Analysis Equipment

Figure 4:
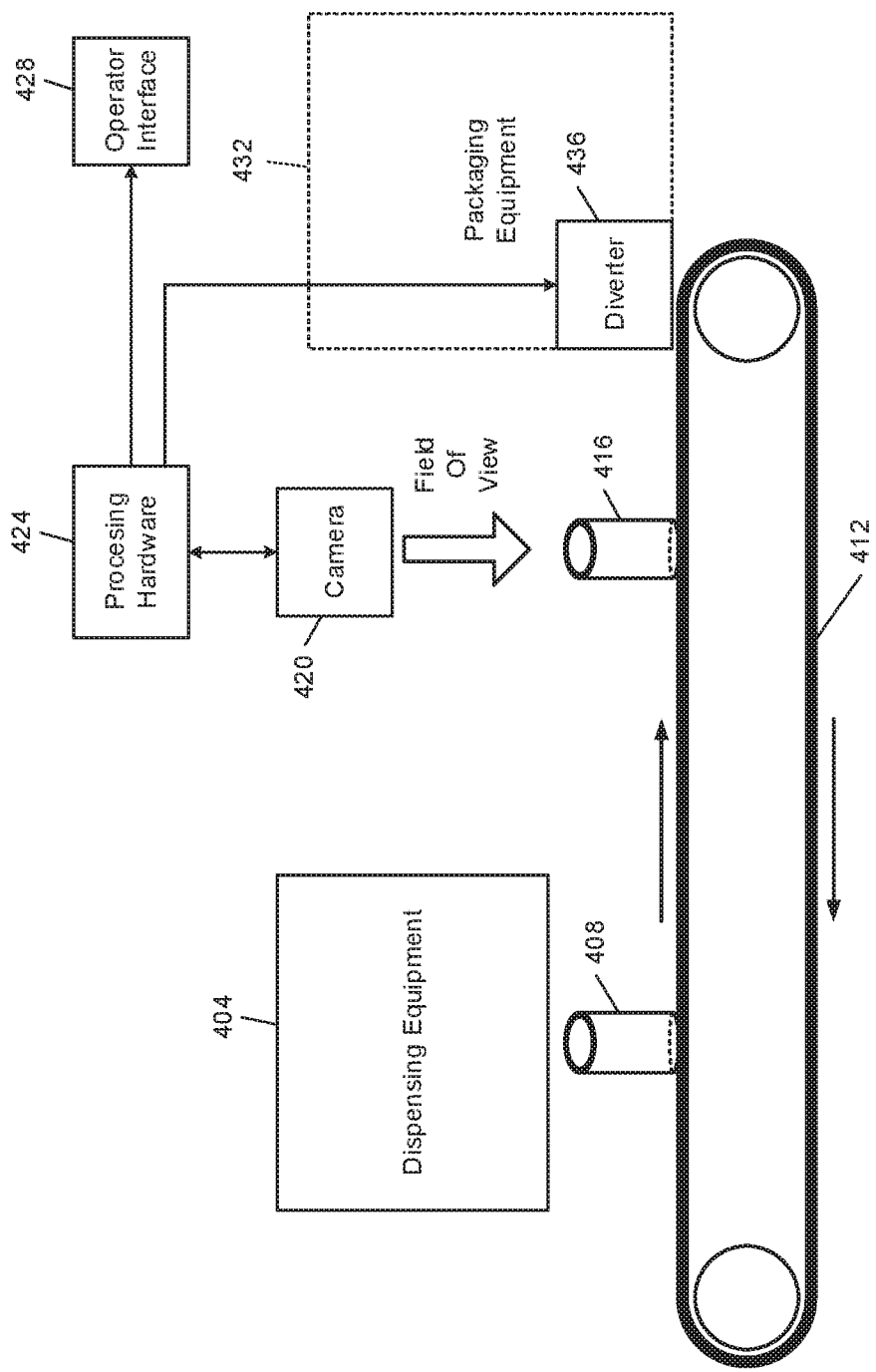
FIG. 4 is a graphical representation of a side view of a hypothetical dispensing system along with a functional block diagram.

In FIG. 4, dispensing equipment 404, such as the automated dispensing device 214, dispenses drugs into a bottle 408. For illustration purposes only, the bottle 408 is positioned on a conveyor 412. A bottle 416 has been moved from underneath the dispensing equipment 404 by the conveyor 412 to a position where a camera 420 can take a picture of the bottle 416. The camera 420 may be implemented by the imaging device 220. In various implementations, the conveyor 412 may stop in order to take a picture. In other implementations, the camera 420 may take a picture when the bottle 416 is located approximately underneath the camera 420.

Processing hardware 424 analyzes the picture to assess whether the correct drugs were dispensed into the bottle 416 and to determine the likelihood that an undesirable drug was included in the bottle 416. If the likelihood of an undesired drug being included or a completely mis-dispensed drug is high enough, the processing hardware 424 may alert an operator interface 428. For example, the operator interface 428 may include a light, a buzzer, or an electronic notification (such as a text message).

Packaging equipment 432 performs various tasks including placing a cap on the bottle 416 and placing the bottle 416 into packaging that can hold multiple bottles. For example, a box may hold a large number of bottles and the box is shipped to a distributor. In other implementations, the packaging equipment 432 packs the bottle 416 along with a small number of other bottles into a single order for delivery to a customer. A diverter 436 may divert the bottle 416 if the processing hardware 424 determines that the bottle 416 may have one or more undesirable drugs. The diverter 436 may move the bottle 416 aside for human observation or may discard the bottle 416. The dispensing equipment 404 may then fill another bottle after the bottle 416 is diverted or may wait for further input from a manual operator.

Example Analysis

Figure 5B:
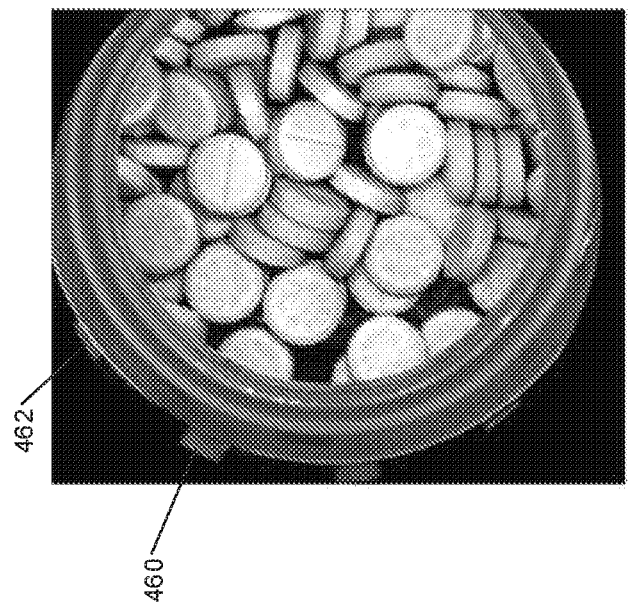
FIG. 5B is an example image once image pre-processing according to the principles of the present disclosure is applied to the image of FIG. 5A.
Figure 5A:
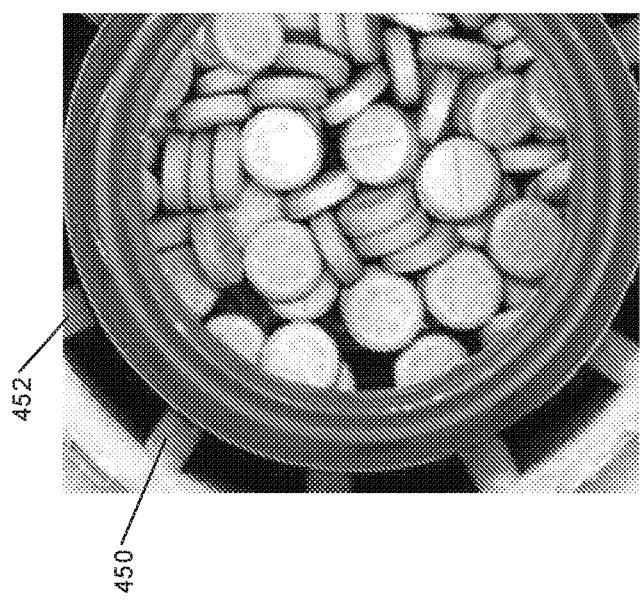
FIG. 5A is an example image prior to pre-processing according to the principles of the present disclosure.

In FIG. 5A, an example image taken of a bottle in plan view, such as by the camera 420 of FIG. 4, is shown. Note that the right-hand side of the bottle is truncated and that plastic ribs associated with the bottle are shown, such as at 450 and 452. After performing preprocessing according to the principles of the present disclosure, an image such as that shown in FIG. 5B may result. Much of the bottle has been removed and the ribs 450, 452 are reduced to stubs 460, 462. This allows image processing to focus on the drugs within the bottle and avoid false positives from the ribs and other components of the bottle.

Figure 6:
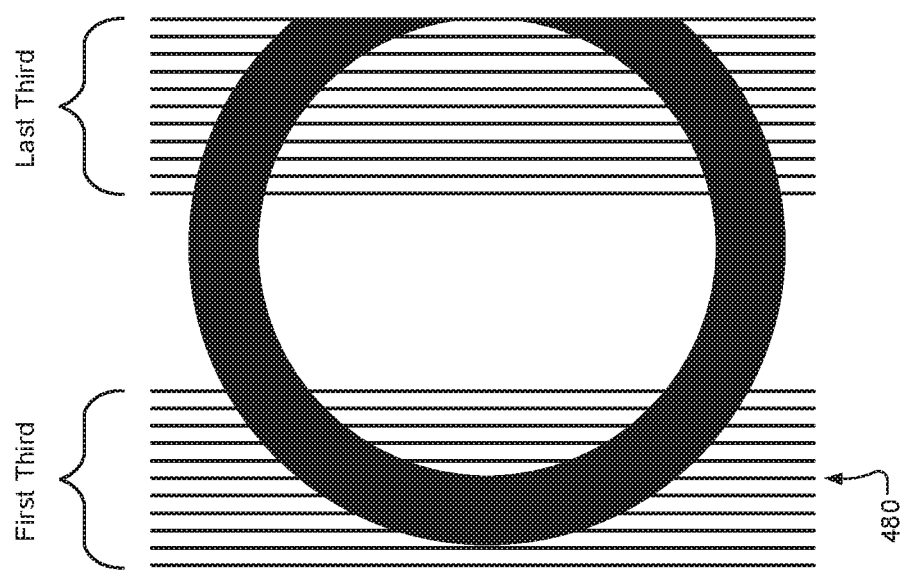
FIG. 6 is graphical example of a slice-by-slice analysis of an image.

In FIG. 6, a simplified graphical representation of image preprocessing is shown. First, the pixels of the image likely to correspond to the bottle are identified. These may be referred to as candidate pixels. As described in more detail below, the darkest 25% of the pixels in the image may be chosen as candidate pixels. In FIG. 6, the candidate pixels are shown and form a partial ring. In a real image, it is unlikely that the candidate pixels would form such a clearly defined ring and, in fact, it would be expected that some of the candidate pixels will not even be contiguous.

On the assumption that the first third of the image along a horizontal axis will include the left side of the bottle and the last third of the image along the horizontal axis will include the right side of the bottle, each column of the image is analyzed separately to count how many of the candidate pixels occur in each column.

When the candidate pixels form a clearly defined ring, as shown in FIG. 6, the column at the inside edge of the ring will have the greatest count of pixels within the first third of the image. This column is approximately indicated by reference numeral 480. The number of the candidate pixels in each column decreases as you move away from the column 480.

Figure 7:
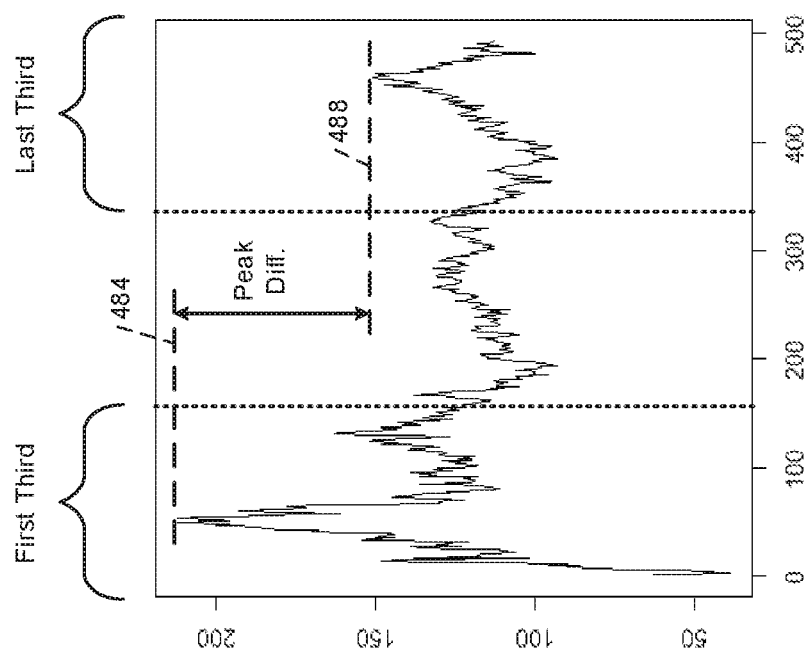
FIG. 7 is a plot of example data acquired by analyzing an image slice-by-slice.

In FIG. 7, a plot shows a count of the number of candidate pixels on the Y-axis with the X-axis being the horizontal coordinate (column number) of the image. In FIG. 7, a peak level 484 is determined for the counts within the left third of the image and a peak level 488 is determined for the counts within the right third of the image. If the difference between the peak levels 484 and 488 is too great, this may be an indication that the side of the image having a lower peak level does not include the edge of the bottle. For example, looking at FIG. 6, the right-hand side of the bottle is missing and, therefore, the peak count of candidate pixels per column is never as high in the right third of the image as in the left third of the image.

Processing Hardware

Figure 8:
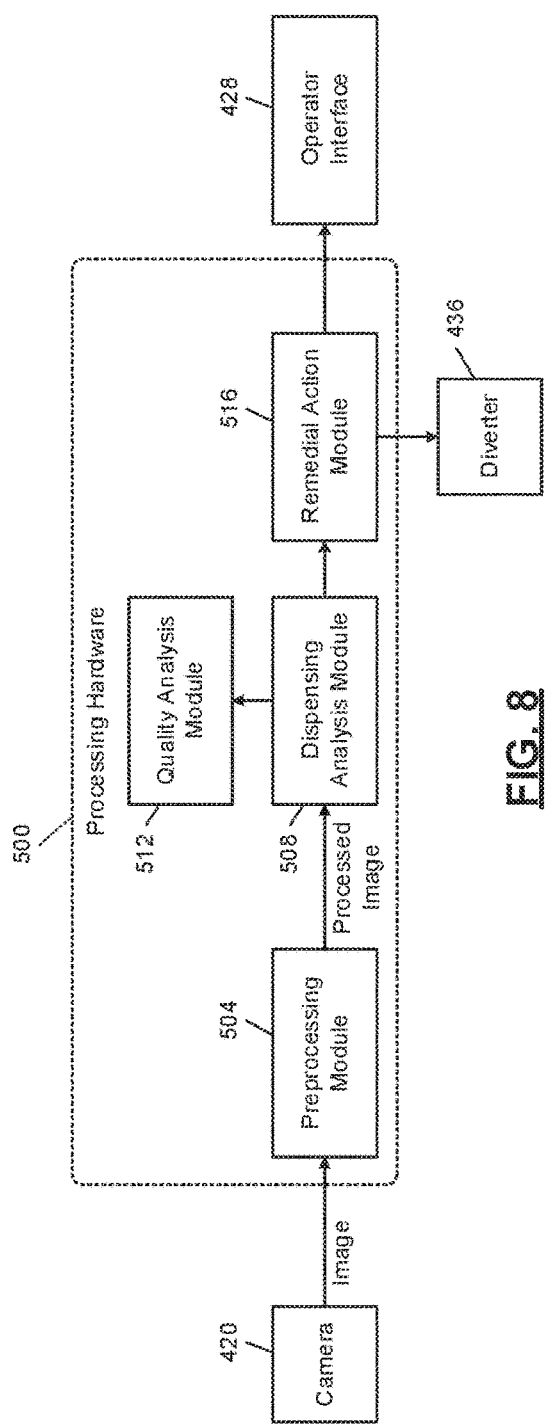
FIG. 8 is a functional block diagram of example processing hardware according to the principles of the present disclosure.

In FIG. 8, a functional block diagram of the processing hardware 500 includes a preprocessing module 504, which receives the image from the camera 420 and provides a processed image to a dispensing analysis module 508. The dispensing analysis module determines whether there is likelihood of a mis-dispensed drug and reports that likelihood to a quality analysis module 512 as well as a remedial action module 516. The quality analysis 512 tracks apparent dispensing errors over time. The remedial action module 516 may actuate the operator interface 428 and/or the diverter 436.

Figure 9:
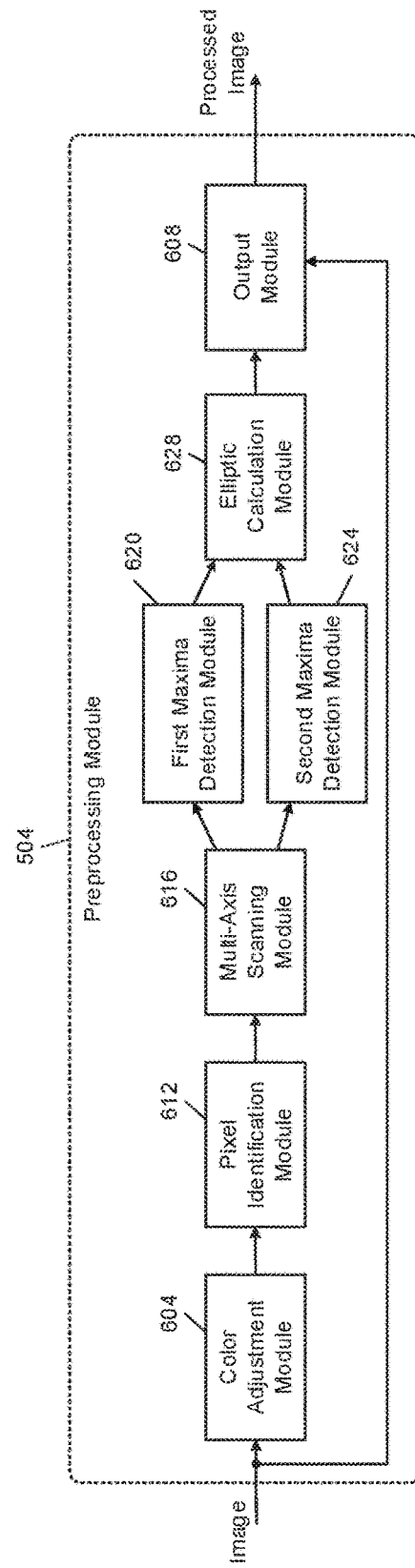
FIG. 9 is a functional block diagram of an example preprocessing module according to the principles of the present disclosure.

In FIG. 9, a functional block diagram of an example implementation of the preprocessing module 504 includes a color adjustment module 604. The color adjustment module 604 receives a copy of the image as does an output module 608. The color adjustment module 604 adjusts the color of the image to make the pill bottle itself easier to identify. For example, the color adjustment module 604 may increase the contrast of the image. In various implementations, the color adjustment module may set the red, green, and blue values of each pixel according to equations described below.

A pixel identification module 612 identifies pixels likely to be part of the bottle based on the color-adjusted image. A multi-axis scanning module 616 outputs counts of these likely pixels along multiples axes. For example, a count of likely pixels for each column of pixels is provided to a first maxima detection module 620 while a count of likely pixels in each row of the image is provided to a second maxima detection module 624.

The first maxima detection module 620 may determine a maximum value within a first region of the image and a maximum value within a second region of the image. These values may be referred to as h1 and h3. For example, when the first maxima detection module 620 analyzes the horizontal axis, the first region may be the left-hand third of the image while the second region may be the right-hand third of the image. The remaining middle third of the image is therefore not analyzed by the first maxima detection module 620.

The second maxima detection module 624 may determine a maximum value within a first region of the image and a maximum value within a second region of the image. These values may be referred to as v1 and v3. For example, when the first maxima detection module 620 analyzes the vertical axis, the first region may be the top third of the image while the second region may be the bottom third of the image. The remaining middle third of the image is therefore not analyzed by the second maxima detection module 624.

An elliptic calculation module 628 defines an ellipse based on the positions of the maxima detected along the first axis by the first maxima detection module 620, which define endpoints of a first axis of the ellipse. The ellipse is also based on positions of the maxima detected along the second axis by the second maxima detection module 624, which define endpoints of a second axis of the ellipse. The longer of the two axes of the ellipse is called the major axis while the shorter of the two axes of the ellipse is called the minor axis.

If the difference between the two maxima values along an axis is greater than a predetermined value, then an assumption may be made that the lower of the maxima is not really the edge of the bottle, and instead the edge of the bottle is at the edge of the image. The endpoint of the corresponding axis of the ellipse would therefore be set to the edge of the image. The predetermined value may be 20% of the greater of the two maxima or may be 20% of the size of the image in the direction perpendicular to the axis.

In various implementations, the ellipse defined by the elliptic calculation module 628 may be a circle—that is, the major and minor axes of the ellipse are equal in length. For example, the elliptic calculation module 628 may average the major and minor axes of the ellipse to determine a diameter of the circle. In other implementations, the elliptic calculation module 628 may select one of the major or minor axes to be a diameter of the circle.

The elliptic calculation module 628 may calculate the boundaries of the ellipse as follows:
Center of bottle x and y coordinates: [(h1+h3)/2, (v1+v3)/2]
Top center edge (T): [(h1+h3)/2, v1]
Bottom center edge (B): [(h1+h3)/2, v3]
Right center edge (R): [h3, (v1+v3)/2] Left
center edge (L): [h1, (v1+v3)/2]
Radius of Bottle (RAD): max[(h1+h3)/2, (v1+v3)/2]
Upper Left Edge: [(h1+h3)/4, (v1+v3)/2−sin(pi/4)*RAD]
Upper Right Edge: [3*(h1+h3)/4, (v1+v3)/2−sin(pi/4)*RAD]
Lower Left Edge: [(h1+h3)/4, (v1+v3)/2+sin(pi/4)*RAD]
Lower Right Edge: [3*(h1+h3)/4, (v1+v3)/2+sin(pi/4)*RAD]

The output module 608 uses the calculated ellipse to adjust a copy of the original image. This adjustment may include creating metadata identifying pixels that should be ignored when processing or may include adjusting the pixels to be ignored. For example, the metadata may be embedded in an image file or may be provided in conjunction with the image file. Adjusting the pixels to be ignored may include setting the pixels to be ignored to a predetermined color, such as black. The output module 608 outputs the processed image to the dispensing analysis module 508 of FIG. 8.

Flowcharts

Figure 10:
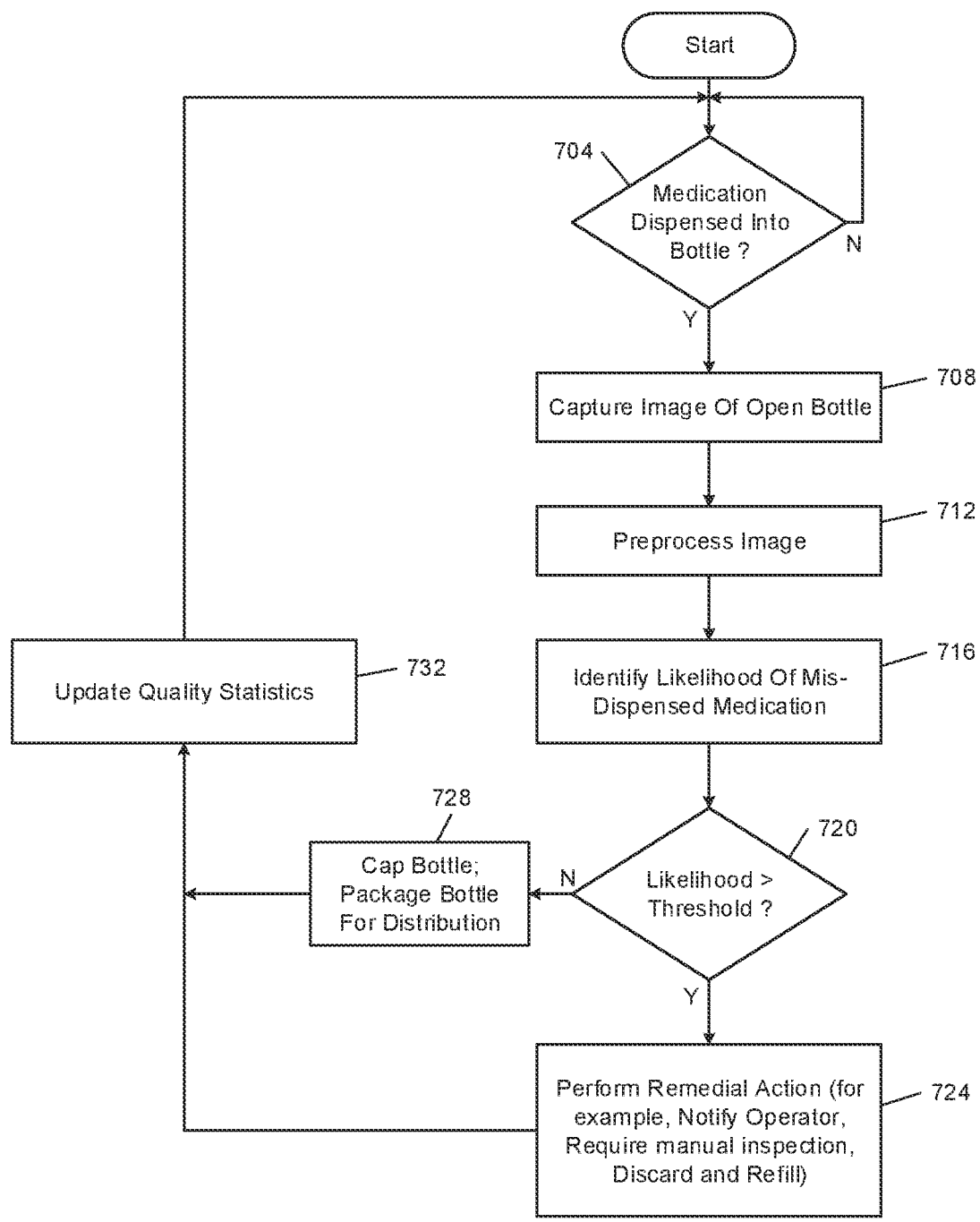
FIG. 10 is a flowchart of high-level pharmacy processing.

In FIG. 10, a flowchart of overall operation of the quality control system is presented. Control begins at 704 where if a medication has been dispensed into a bottle, control continues at 708; otherwise, control remains at 704. At 708, control captures an image from above of the open bottle. At 712, control preprocesses the image, such as by removing regions outside of the bottle.

At 716, control identifies the likelihood of mis-dispensed medication based on processing of the preprocessed image. For example, a machine learning (ML) model such as a convolutional neural network (CNN) is first trained on images of pills, which captures characteristics such as color, shape, size, and markings. The images may be high resolution images of single pills taken at different orientations of the pills. The preprocessed image is then provided to the trained CNN to identify which pills are present inside of the bottle.

At 720, if the likelihood of mis-dispensed medication is greater than a predetermined threshold, control transfers to 724; otherwise, control transfers to 728. The trained CNN may output a set of probabilities indicating the likelihood that the respective pills are present in the bottle according to the preprocessed image. For example, the trained CNN may output the 5 most likely pills present in the image as well as the respective probabilities that the pill is actually present.

In another implementation, the CNN may have been trained to recognize N pills (as one example, N may be 1500) and output an N-dimensional vector, with each element of the vector indicating a likelihood of the corresponding pill being present in the bottle. Based on the prescription that controlled the pill dispense, a reference vector may be created with a 1.0 value (indicating 100% likelihood of presence) for the prescribed pill and zero values for the remaining N−1 elements of the vector. If the difference between the reference vector and the vector output form the CNN is greater than a predetermined distance threshold, control may determine that the likelihood of mis-dispensed medication is sufficiently great to trigger remedial action.

At 724, control performs remedial action based on the potential for a mis-dispensed mediation. For example, the remedial action may include notifying an operator, forcing a manual inspection of the bottle, and/or discarding and refilling the bottle.

Control then continues at 732. At 732, quality statistics are updated based on the identified likelihood of a mis-dispensed medication as well as based on any feedback from the manual inspection. These quality statistics may be used to judge false positives in the image processing as well as to identify problems with the dispensing equipment. Control then returns to 704. At 728, control caps the bottle and packages the bottle for distribution. Control then continues at 732.

Figure 11A:
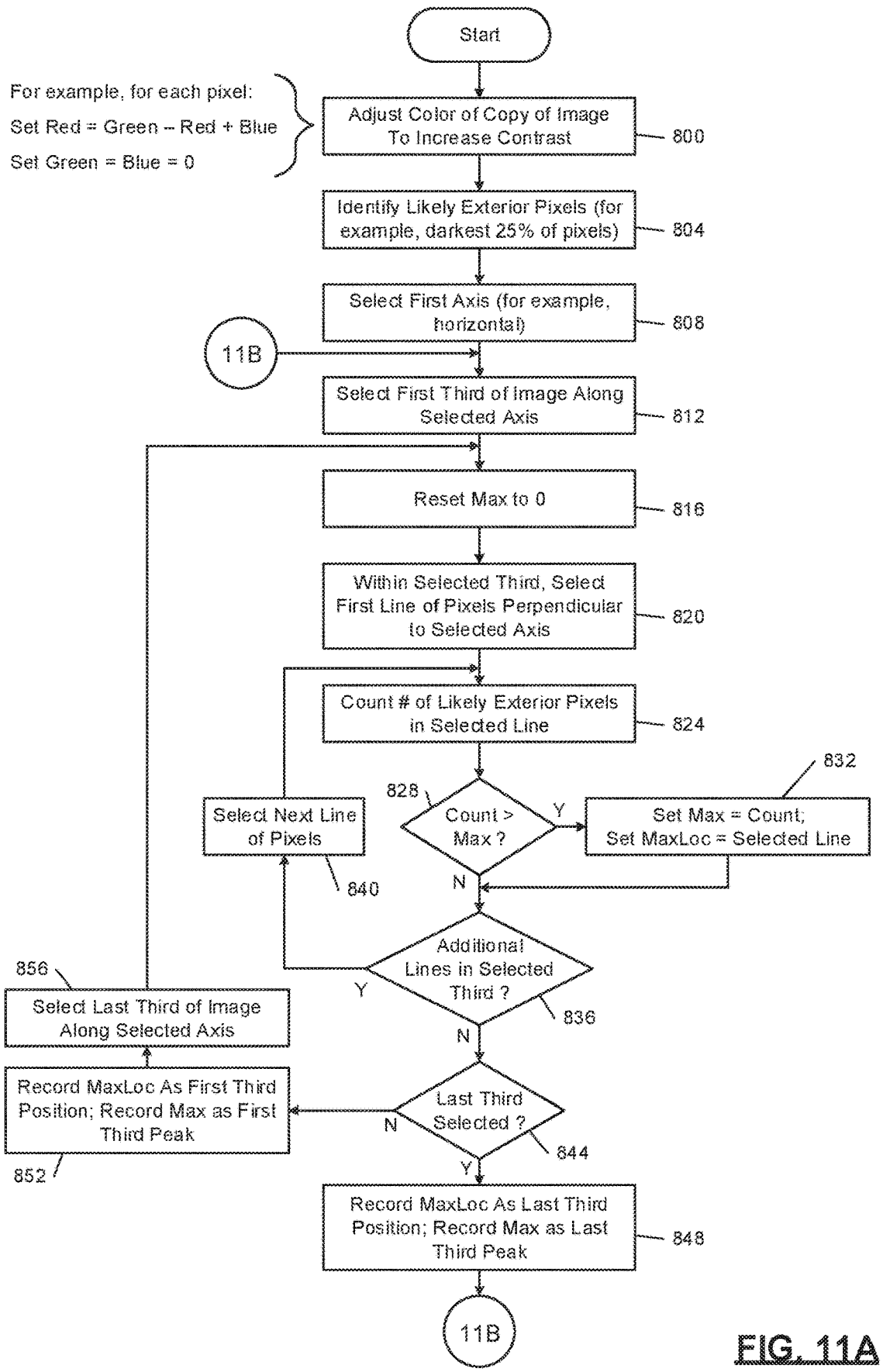
FIGS. 11A and 11B together form a flowchart of example preprocessing operation according to the principles of the present disclosure.
Figure 11B:
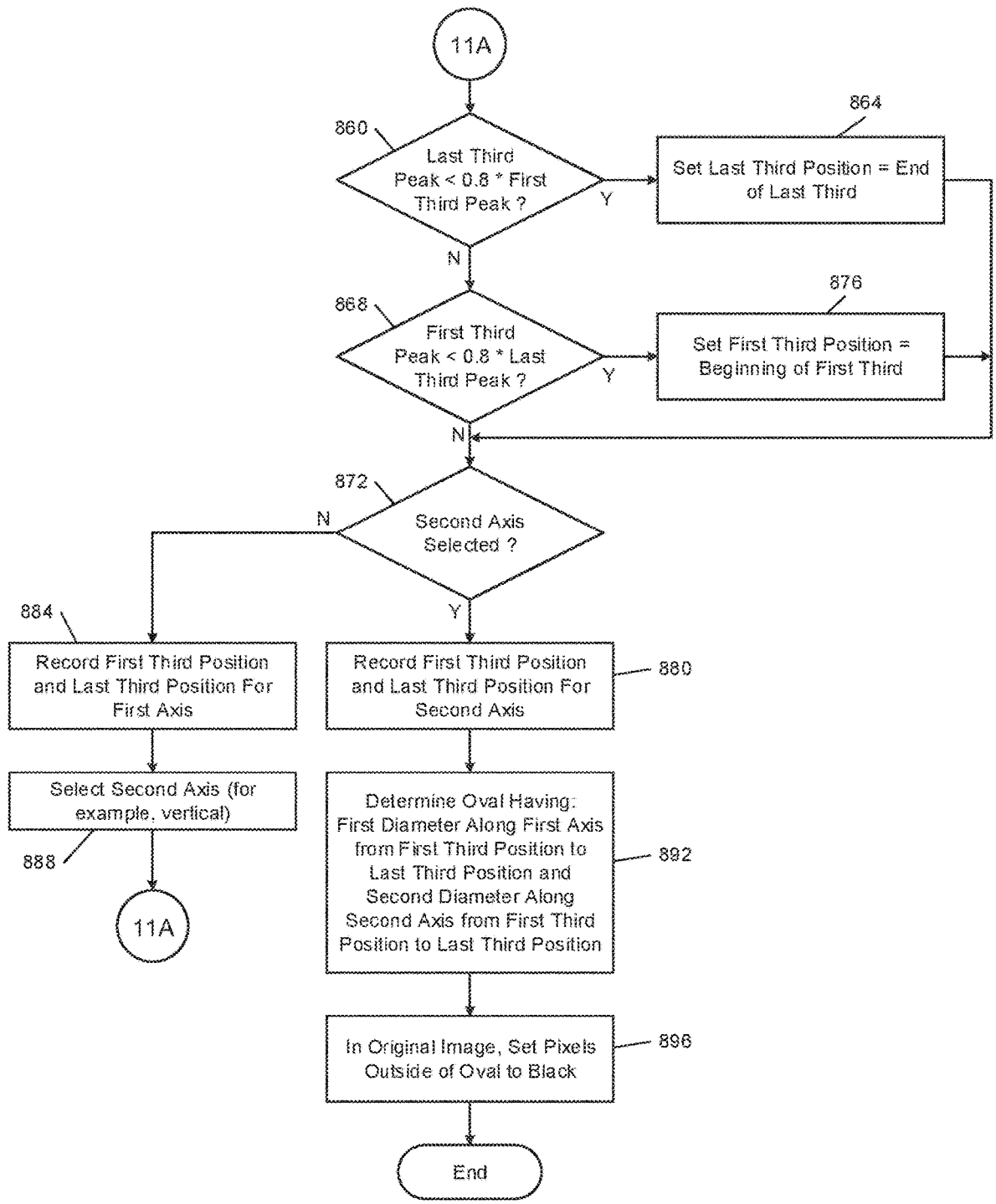

FIGS. 11A and 11B together form a flowchart of example operation of preprocessing according to the principles of the present disclosure. Control begins in FIG. 11A at 800 when an image to be preprocessed is received. At 800, control adjusts the color of a copy of the image to increase contrast. For example, for each pixel, the red component of the pixel may be set equal to the sum of the green and blue values minus the red value, while the green and blue values are both set to zero. In other words, the color of the pixel is reduced to a single value, encoded in the red channel. A single value for color may also be referred to as grayscale, with the size of the value indicating how bright the pixel is on a black-to-white continuum.

At 804, control identifies the pixels that are most likely to be the exterior of the bottle. For example, all of the pixels in the image may be ordered by how dark they are and the darkest 25% of the pixels may be identified as the likely exterior pixels. At 808, control selects a first axis. For example, and as was shown in FIG. 6, the first axis may be the horizontal axis. In other implementations, the first axis is the vertical axis or an axis that is not perpendicular to either the horizontal or vertical axis. At 812, control selects the first third of the image along the selected axis. For example, when the selected axis is a horizontal axis, the first third of the image may be defined to be the left-hand third of the image.

At 816, control resets a variable named Max to 0. At 820, within the selected third of the image, control selects the first line of pixels perpendicular to the selected axis. As an example, if the selected third is the left-hand third of the image, the first line of pixels is the leftmost column of pixels. At 824, control counts the number of likely exterior pixels in the selected line. At 828, if the count is greater than the current value of Max, control transfers to 832; otherwise, control transfers to 836. Because Max was reset to 0 at 816, the first count will become the next Max. At 832, the variable Max is set to be equal to the count and a variable MaxLoc (corresponding to the location of the maximum) is set equal to the number of the selected line. Control then continues at 836.

At 836, if there are additional lines in the selected third of the image, control transfers to 840; otherwise control transfers to 844. At 840, control selects the next line of pixels and continues at 824. At 844, if the last third of the image is already selected, control transfers to 848; otherwise, control transfers to 852. At 852, the last third of the image was not selected, meaning that the first third of the image had been selected. Therefore, the value of MaxLoc is recorded as the position of interest for first third and value of Max is recorded as the peak within the first third of the image.

Control then continues at 856, where control selects the last third of the image along the selected axis. Control then continues at 816.

At 848, the last third of the image had been selected and therefore the value of MaxLoc is recorded as the position of interest for the last third of the image and the value of Max is recorded as the peak of the last third of the image. Control then continues at 860 in FIG. 11B. At 860, control determines whether the peak of the last third of the image is less than 80% of the peak of the first third of the image. If so, control transfers to 864 to handle this discrepancy; otherwise, control transfers to 868. At 864, the relatively small value for the last third peak suggests that the edge of the bottle is not present within the last third of the image. Therefore, the edge of the bottle is assumed to be at the very end of the last third, and the last third position is set to be the end of the last third of the image. Control then continues at 872.

At 868, control determines whether the peak of the first third of the image is less than 80% of the peak of the last third of the image. If so, control transfers to 876 to handle the discrepancy; otherwise, control transfers to 872. At 876, the relative smallness of the first third peak indicates that the edge of the bottle is outside of the first third of the image and, therefore, the position of interest for the first third is set to be the very beginning of the first third of the image. Control then continues at 872.

At 872, if the second axis is selected, control transfers to 880; otherwise, control transfers to 884. At 884, the second axis has not yet been selected and, therefore, the first third position and the last third position are recorded with respect to the first axis. These positions correspond to the determined edges of the bottle along the first axis. Control continues at 888, where the second axis (such as the vertical axis) is selected. Control then returns to 812 in FIG. 11A

At 880, the second axis has been selected and, therefore, the first third position and last third position are recorded for the second axis. These values correspond to the determined edges of the bottle along the second axis. Control continues at 892, where control determines a mathematically defined ellipse having a first diameter along the first axis from the first third position to the last third position determined for the first axis. The ellipse also has a second diameter along the second axis from the first third position to the last third position determined for the second axis. Control continues at 896, where the mathematically defined ellipse is used to mask out regions of the original image to be excluded from further processing. For example, all pixels outside of the defined ellipse within the original image may be set to black. Control then ends.

Example Machine

Figure 12:
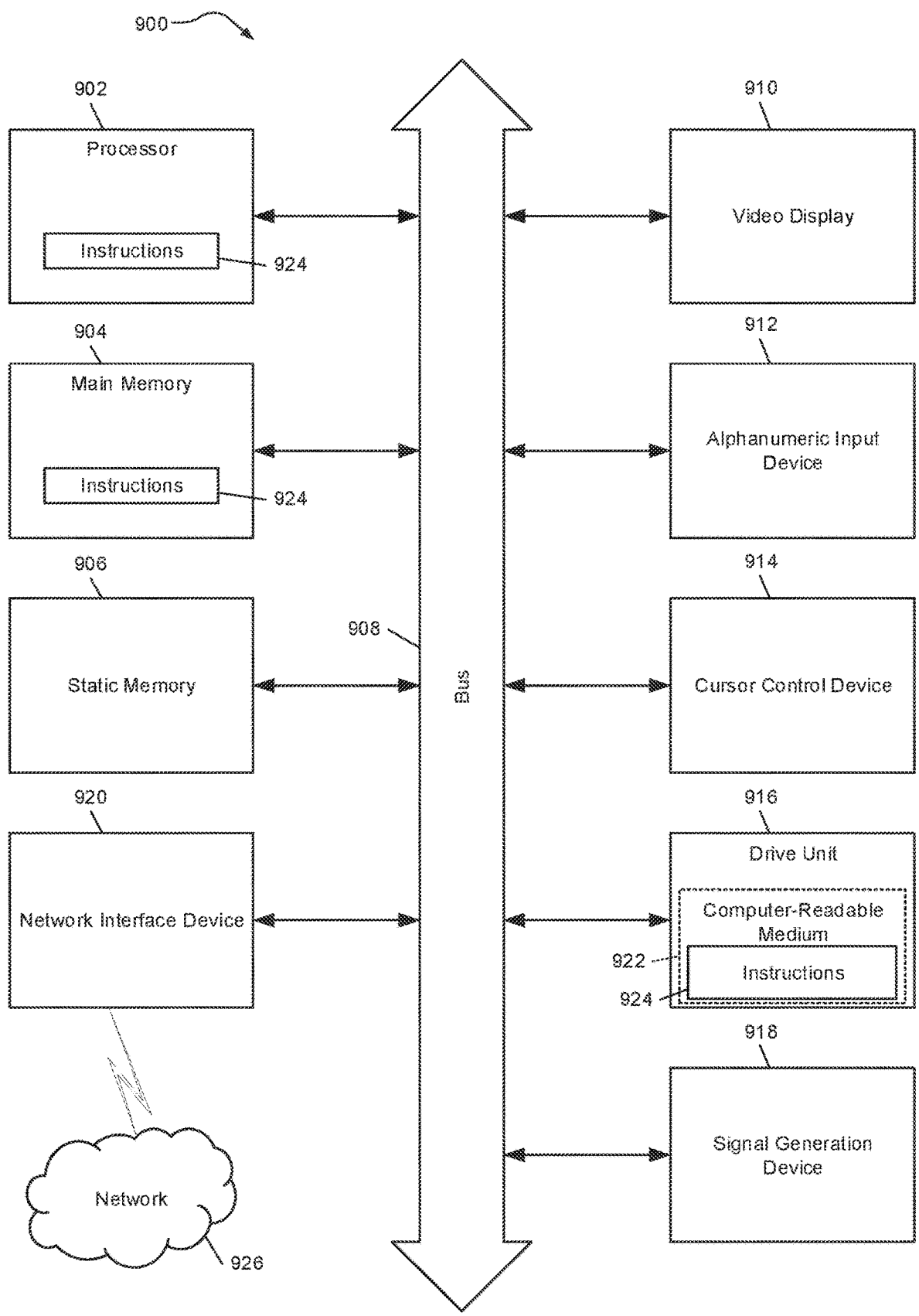
FIG. 12 is a functional block diagram of a machine in the example form of a computer system within which a set of processor-executable instructions for causing the machine to perform methodologies discussed herein may be executed or stored.

FIG. 12 shows a block diagram of a dedicated machine in the example form of a computer system 900 within which a set of instructions may be executed causing the machine to perform any one or more than one methods, processes, operations, or methodologies discussed herein. The devices 206-232, for example, may include the functionality of the one or more than one computer systems 900. These devices and systems are dedicated to performing any one or more than one methods, processes, operations, or methodologies discussed herein.

In an example embodiment, the machine operates as a standalone device or may be connected (e.g., networked, etc.) to other machines. In a networked deployment, the machine may operate in the capacity of a server or a client machine in server-client network environment, or as a peer machine in a peer-to-peer (or distributed) network environment.

The example computer system 900 includes a processor 902 (e.g., a central processing unit (CPU), a graphics processing unit (GPU) or both, etc.), a main memory 904, and a static memory 906, which communicate with each other via a bus 908. The computer system 900 further includes a video display unit 910 (e.g., a liquid crystal display (LCD) or a cathode ray tube (CRT), etc.). The computer system 900 also includes an alphanumeric input device 912 (e.g., a keyboard, etc.), a cursor control device 914 (e.g., a mouse, etc.), a drive unit 916, a signal generation device 918 (e.g., a speaker, etc.), and a network interface device 920.

The drive unit 916 includes a computer-readable medium 922 on which is stored one or more than one sets of instructions (e.g., instructions 924, etc.) embodying any one or more than one methodologies or functions described herein. The instructions 924 may also reside, completely or at least partially, within the main memory 904 and/or within the processor 902 during execution thereof by the computer system 900, the main memory 904 and the processor 902 also constituting non-transitory computer-readable media. When loaded with the instructions 924, the processor 902 is a machine dedicated to only the present processes and methodologies. The instructions 924 may further be transmitted or received over a network 926 via the network interface device 920.

CONCLUSION

In the foregoing detailed description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the detailed description, with each claim standing on its own as a separate embodiment.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

The term "based on" or "using," as used herein, reflects an open-ended term that can reflect other elements beyond those explicitly recited. The present disclosure makes reference to a robot and words of similar import. A robot can be a machine capable of carrying out a complex series of actions automatically. These complex series of actions may include picking up, orientating, positioning, and/or releasing a prescription component, a pill, a container, or other structure. The robot may be dedicated to a single series of movements or may be able to execute multiple series of movements. A robot may include a processor that received instructions and then executes instructions to control its movement. In another example, a robot may resemble a human being and replicate certain human movements and functions, may move location, have an articulated arm, have grasping structures that replicate fingers and do not damage containers, etc.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A Further, for information sent from element A to element B, element B may send requests for, or receipt acknowledgements of, the information to element A In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

The invention claimed is:

1. A computer system comprising:
 an input configured to receive a first image of medication located in a receptacle captured by a camera;

memory configured to store computer-executable instructions; and at least one processor configured to execute the computer-executable instructions, wherein the instructions include:

creating a second image in which each pixel of the second image is based on a corresponding pixel of the first image;

dividing pixels of the second image into a first subset and a second subset such that pixels of the first subset include candidate pixels corresponding to the receptacle;

scanning the second image along a first axis to count, for each point along the first axis, a number of pixels in the first subset along a line perpendicular to the first axis that intersects the first axis at the point;

defining an ellipse, by:
estimating a position of a first edge of the receptacle along the first axis based on the counts of the pixels at each point along the first axis; and
estimating a position of a second edge of the receptacle along the first axis based on the counts of the pixels at each point along the first axis;

defining an opening of the receptacle based on the ellipse, including the estimated positions of the first edge of the receptacle and the second edge of the receptacle;

outputting a processed image that indicates areas that are outside of the defined opening; and identifying a likelihood of mis-dispensed medication based on the processed image.

2. The computer system of claim 1, wherein the opening is defined as an ellipse.

3. The computer system of claim 1, wherein:
the instructions include analyzing the medication based on the processed image; and
the areas of the processed image that are outside of the defined opening are excluded from the analysis.

4. The computer system of claim 1, wherein the instructions include identifying the likelihood of mis-dispensed medication according to at least one of a color of the medication in the processed image, a shape of the medication in the processed image, a size of the medication in the processed image, and markings of the medication in the processed image.

5. The computer system of claim 4, wherein the instructions include, in response to the identified likelihood of mis-dispensed medication being above a threshold:
performing a remedial action including at least one of notifying an operator,
requesting a manual inspection of the receptacle, and discarding the receptacle; and
updating quality statistics based on at least one of the identified likelihood of mis-dispensed medication and feedback from the manual inspection.

6. The computer system of claim 4, wherein the instructions include, in response to the identified likelihood of mis-dispensed medication being below a threshold, capping and packaging the receptacle for distribution.

7. The computer system of claim 1 wherein creating the second image includes, for each pixel of the second image, generating the pixel by adjusting at least one value of the corresponding pixel of the first image.

8. The computer system of claim 7, wherein creating the second image includes, for each pixel of the second image, generating the pixel by calculating a grayscale value of the corresponding pixel of the first image.

9. The computer system of claim 7, wherein creating the second image includes, for each pixel of the second image, generating the pixel by:
setting a green value of the pixel to a sum of (i) a green value of the corresponding pixel of the first image and (ii) a blue value of the corresponding pixel of the first image minus (iii) a red value of the corresponding pixel of the first image;
setting a green value of the pixel to zero; and
setting a blue value of the pixel to zero.

10. The computer system of claim 1, wherein:
estimating the position of the first edge of the receptacle includes determining a first local maximum of the counts of the pixels at each point along the first axis; and
estimating the position of the second edge of the receptacle includes determining a second local maximum of the counts of the pixels at each point along the first axis.

11. The computer system of claim 10, wherein the instructions include, in response to the second local maximum being less than the first local maximum by more than a predetermined amount, estimating the position of the second edge of the receptacle to be an edge of the first image.

12. The computer system of claim 1, wherein the instructions include:
scanning the second image along a second axis to count, for each point along the second axis, a number of pixels in the first subset along a line perpendicular to the second axis that intersects the second axis at the point;
estimating a position of a third edge of the receptacle along the second axis based on the counts of the pixels at each point along the second axis; and
estimating a position of a fourth edge of the receptacle along the second axis based on the counts of the pixels at each point along the second axis.

13. The computer system of claim 12, wherein:
the first axis is parallel to a first edge of the first image; and
the second axis is perpendicular to the first axis.

14. A vision system comprising:
the computer system of claim 1; and
the camera.

15. A method of image pre-processing for automated medication dispensing, the method comprising:
receiving a first image of medication located in a receptacle captured by a camera;
creating a second image in which each pixel of the second image is based on a corresponding pixel of the first image;
dividing pixels of the second image into a first subset and a second subset such that pixels of the first subset include candidate pixels corresponding to the receptacle;
scanning the second image along a first axis to count, for each point along the first axis, a number of pixels in the first subset along a line perpendicular to the first axis that intersects the first axis at the point;
defining an ellipse, by:
estimating a position of a first edge of the receptacle along the first axis based on the counts of the pixels at each point along the first axis; and
estimating a position of a second edge of the receptacle along the first axis based on the counts of the pixels at each point along the first axis;
defining an opening of the receptacle based on the ellipse, including the estimated positions of the first edge of the receptacle and the second edge of the receptacle;

outputting a processed image that indicates areas that are outside of the defined opening; and identifying a likelihood of mis-dispensed medication based on the processed image.

16. The method of claim 15, further comprising identifying the likelihood of mis-dispensed medication according to at least one of a color of the medication in the processed image, a shape of the medication in the processed image, a size of the medication in the processed image and markings of the medication in the processed image.

17. The method of claim 16, further comprising, in response to the identified likelihood of mis-dispensed medication being above a threshold:

performing a remedial action including at least one of notifying an operator, requesting a manual inspection of the receptacle, and discarding the receptacle; and updating quality statistics based on at least one of the identified likelihood of mis-dispensed medication and feedback from the manual inspection.

18. The method of claim 16, further comprising, in response to the identified likelihood of mis-dispensed medication being below a threshold, capping and packaging the receptacle for distribution.

19. The method of claim 15, wherein:

estimating the position of the first edge of the receptacle includes determining a first local maximum of the counts of the pixels at each point along the first axis; and estimating the position of the second edge of the receptacle includes determining a second local maximum of the counts of the pixels at each point along the first axis.

20. The method of claim 15, further comprising:

scanning the second image along a second axis to count, for each point along the second axis, a number of pixels in the first subset along a line perpendicular to the second axis that intersects the second axis at the point;

estimating a position of a third edge of the receptacle along the second axis based on the counts of the pixels at each point along the second axis; and estimating a position of a fourth edge of the receptacle along the second axis based on the counts of the pixels at each point along the second axis.

* * * * *